United States Patent
Misra

(10) Patent No.: US 11,571,449 B2
(45) Date of Patent: Feb. 7, 2023

(54) PHARMACEUTICAL COMPOSITION COMPRISING A COMBINATION OF PROBIOTIC AND PREBIOTIC TO TREAT STUNTING

(71) Applicant: CHR. HANSEN A/S, Hoersholm (DK)

(72) Inventor: Pravas Ranjan Misra, Odisha (IN)

(73) Assignee: Chr. Hansen A/S, Hoersholm (DK)

( * ) Notice: Subject to any disclaimer, the term of this patent is extended or adjusted under 35 U.S.C. 154(b) by 18 days.

(21) Appl. No.: 16/652,059

(22) PCT Filed: Oct. 4, 2018

(86) PCT No.: PCT/IB2018/057721
§ 371 (c)(1),
(2) Date: Mar. 29, 2020

(87) PCT Pub. No.: WO2019/069267
PCT Pub. Date: Apr. 11, 2019

(65) Prior Publication Data
US 2020/0246402 A1 Aug. 6, 2020

(30) Foreign Application Priority Data
Oct. 4, 2017 (IN) .............................. 201731035101

(51) Int. Cl.
*A61K 35/747* (2015.01)
*A61K 31/702* (2006.01)
*A61K 9/00* (2006.01)

(52) U.S. Cl.
CPC .......... *A61K 35/747* (2013.01); *A61K 9/0029* (2013.01); *A61K 9/0053* (2013.01); *A61K 31/702* (2013.01)

(58) Field of Classification Search
CPC .............. A61K 2300/00; A61K 31/702; A61K 31/715; A61K 31/723; A61K 31/732; A61K 35/747; F16C 19/386
See application file for complete search history.

(56) References Cited

U.S. PATENT DOCUMENTS

| 7,101,565 B2 * | 9/2006 | Monte | ................... | A61K 35/745 424/423 |
| 2015/0250833 A1 * | 9/2015 | Rubio Nistal | ......... | A61K 45/06 424/93.45 |
| 2020/0246402 A1 | 8/2020 | Misra | | |

FOREIGN PATENT DOCUMENTS

| WO | 2012108830 A1 | 8/2012 |
| WO | WO-2014/178007 A2 | 11/2014 |
| WO | 2019069266 A1 | 4/2019 |
| WO | 2019069267 A1 | 4/2019 |

OTHER PUBLICATIONS

Firmansyah et al "Improved growth of toddlers fed a milk containing synbiotics", Asia Pac. J. of Clinical Nutr. Mar. 1, 2001; 20(1): 69-76. (Year: 2011).*
Panigrahi et al A randomized synbiotic trial to prevent sepsis among infants in rural India. Nature. Aug. 2017; 548(7668): 407. (Year: 2017).*
Panigraahi et al. "Long-term Colonization of a Lactobacillus plantarum Synbiotic Preparation in the Neonatal Gut", J. of Pediatric Gastroenterlogy and Nutrition; 47:45-53, 2008. (Year: 2008).*
PCT International Search Report and Written Opinion for application No. PCT/IB2018/057720 dated Feb. 13, 2019.
PCT International Search Report and Written Opinion for application No. PCT/IB2018/057721 dated Jan. 23, 2019.
Blanton et al. Gut bacteria that prevent growth impairments transmitted by microbiota from malnourished children. Science. Feb. 19, 2016;351(6275). pii: aad3311. doi: 10.1126/science.aad3311. PubMed PMID: 26912898.
Guimaraes et al, Genetic detection of extended-spectrum β-lactamase-containimg *Escherichia coli* isolates and vancomycin-resistant Enterococci in fecal samples of healthy children. Microb Drug Res. 2009, 15(3):211-216.
Jacoby G A, Munoz-Price L S: The new β-lactamases. N Eng J Med. 2005, 352:380-391).
Lebessi et al, Extended-spectrum β-lactamase-producing Klebsiella pneumonia in a neonatal intensive care unit in the high-prevalence area of Athens, Greece. J Clin Microbiol. 2002, 40:99-804.
Monstein et al., Multiplex PCR amplification assay for the detection of blaTEM, blaSHV and blaCTX-M genes in Enterobacteriaceae. APMIS 2007, 115: 1400-08.
Pitout et al The latest threat in the war on antimicrobial resistance. Lancet Infect Dis. 2010, 10:578-9.
Price et al Clinical epidemiology of the global expansion of Klebsiella pneumoniae carbapenemases. Lancet Infect Dis. 2013, 13:185-96.
Rahman et al, High rates of intestinal colonization with extended-spectrum lactamase-producing Enterobacteriacae among healthy individuals. J Investig Med. 2011, 59:1284-1286.
Royle et al, Outbreak of extended spectrum beta lactamase producing Klebsiella pneumoniae in a neonatal unit. Arch Dis Child Fetal Neonatal Ed. 1999, 80:F64-8.
Venezia et al, Molecular epidemiology of an SHV-5 extended-spectrum beta-lactamase in enterobacteriaceae isolated from infants in a neonatal intensive care unit. Clin Infect Dis. 1995, 21:915-23.
Asahara et al, Protective effect of Lactobacillus casei strain Shirota against lethal infection with multi-drug resistant *Salmonella enterica* serovar Typhimurium DT104 in mice. J Appl Microbiol. 2011, 110:163-73.

(Continued)

*Primary Examiner* — David W Berke-Schlessel
(74) *Attorney, Agent, or Firm* — Foley & Lardner LLP

(57) ABSTRACT

The present invention provides a pharmaceutical composition including a probiotic and a prebiotic for treatment of stunting in children. More particularly, the pharmaceutical composition includes at least one *Lactobacillus* specie(s) as a probiotic and at least one oligosaccharide as a prebiotic. The present invention further provides a method of treatment of stunting including administering an effective amount of a pharmaceutical composition including a probiotic and a prebiotic to children in need thereof.

9 Claims, No Drawings

(56) References Cited

OTHER PUBLICATIONS

Ben-Ami et al, A multinational survey of risk factors for infection with extended-spectrum β-lactamase-producing Enterobacteriaceae in nonhospitalized patients. Clin Infect Dis. 2009, 49:682-90.

Bertrand et al, Effect of cheese consumption on emergence of antimicrobial resistance in the intestinal microflora induced by a short course of amoxicillin-clavulanic acid. J Appl Microbiol. 2007, 102:1052-9.

Cartelle et al, Risk factors for colonization and infection in a hospital outbreak caused by a strain of Klebsiella pneumoniae with reduced susceptibility to expanded-spectrum cephalosporins. J Clin Microbiol. 2004, 42:4242-4249.

Chandel et al, Extended-spectrum β-lactamase-producing Gram-negative bacteria causing neonatal sepsis in India in rural and urban settings. J Medical Micro. 2011, 60:500-507.

Isendahl et al, Fecal carriage of ESBL-producing *E. coli* and K. pneumonia in children in Guinea-Bissau: A hospital-based cross-sectional study. PLoS One. 2010, 7(12) e51981.

Jain et al, Prevalence of extended-spectrum b-lactamase-producing Gram-negative bacteria in septicaemic neonates in a tertiary care hospital. J Med Microbiol. 2003, 52: 421-425.

Jemima et al Multiplex PCR for blaCTX-M & blaSHV in the extended spectrum beta lactamase (ESBL) producing Gram-negative isolates. Indian J Med Res. 2008, 128:313-317.

Jiang et al, Detection of extended-spectrum β-lactamases in clinical isolates of Pseudomonas aeruginosa. Antimicrob Ag Chemother. 2006, 50:2990-2995.

Kothari et al, Community acquisition of β-lactamase producing Enterobateriaceae in neonatal gut. BMC Microbiology. 2013, 13:136-141.

Kumarasamy et al Emergence of a new antibiotic resistance mechanism in India, Pakistan, and the UK: a molecular, biological, and epidemiological study. Lancet Infect Dis. 2010, 10:597-602.

Lal et al, Occurrence of TEM & SHV gene in extended spectrum β-lactamases (ESBLs) producing *Klebsiella* sp. isolated from a tertiary care hospital. Indian J Med Res. 2007, 125:173-178.

Lautenbach et al Epidemiological investigation of fluoroquinolone resistance in infections due to extended spectrum β-lactamase-producing *Escherichia coli* and Klebsiella pneumonia. Clin Infect Dis. 2001, 33:1288-1294.

Luvsansharav et al, Prevalence of risk factors associated with fecal carriage of CTX-M β-lactamase-producing Enterobacteriaceae in rural Thai communities. J Antimicrob Chemother. 2012, 67:1769-1774.

Naylor et al., Environmental Enteropathy, Oral Vaccine Failure and Growth Faltering in Infants in Bangladesh. E Bio Medicine. Sep. 25, 2015;2(11):1759-66. doi: 10.1016/j.ebiom.2015.09.036. eCollection Nov. 2015.

Pallecchi et al, Detection of CTX-M-type β-lactamase genes in fecal *Escherichia coli* isolates from healthy children in Bolivia and Peru. Antimicrob Agents Chemother. 2004, 48(12): 4556-4561.

Saavedra J M, Clinical applications of probiotic agents. Am J Clin Nutr. 2001, 73:1147S-1151S.

Yong et al Characterization of a new metallo-beta-lactamase gene, bla(NDM-1), and a novel erythromycin esterase gene carried on a unique genetic structure in Klebsiella pneumoniae sequence type 14 from India. Antimicrob Agents Chemother. 2009, 53:5046-5054.

Chandel, Dinesh S. et al.; "Changes in the gut microbiota after early administration of oral synbiotics to young infants in India"; J Pediatr Gastroenterol Nutr. Aug. 2017; 65(2): 218-224.

Onubi, Ojochenemi J. et al.; "Effects of probiotics on child growth: a systematic review"; Journal of Health, Population and Nutrition (2015) 34:8; May 2015; 15 pages.

Saran, Shailee et al.; "Use of Fermented Foods to Combat Stunting and Failure to Thrive"; Nutrition, vol. 18, No. 5; May 2002; pp. 393-396.

\* cited by examiner

PHARMACEUTICAL COMPOSITION COMPRISING A COMBINATION OF PROBIOTIC AND PREBIOTIC TO TREAT STUNTING

FIELD OF THE INVENTION

The present invention relates to a pharmaceutical composition including a probiotic and a prebiotic for treating stunting. More particularly, the present invention relates to a composition including at least one *Lactobacillus* specie(s) as a probiotic and at least one oligosaccharide as a prebiotic for treating stunting in children. The present invention also relates to methods of treatment of stunting in children.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Short stature or stunted growth refers to children whose height or rate of height gain is lower than other children of the same age and gender. Stunting is defined as the percentage of children, aged 0 to 59 months, whose height for age is below minus two standard deviations (moderate and severe stunting) and minus three standard deviations (severe stunting) from the median of the WHO Child Growth Standards.

Stunting is not a growth disorder, and is often associated with malnutrition. It is a primary manifestation of malnutrition or under-nutrition and recurrent infections, such as diarrhea, in early childhood. Stunting may start from pre-conception in an adolescent girl and who later becomes mother is undernourished and anaemic; it worsens when infants' diets are poor, and when sanitation and hygiene is inadequate. It is irreversible by the age of two. Child survival and health is inseparably connected to reproductive and, maternal health.

The world health organization estimates that 165 million of the world's children are stunted and majority of them are from developing countries. Children in such countries grow up under poor hygienic conditions, multiple episodes of gastrointestinal infections, with poor nutrition. This results in suboptimal physical growth, under developed brain, with long-lasting harmful consequences, including diminished mental ability and learning capacity, poor school performance in childhood, reduced earnings and increased risks of nutrition related chronic diseases, such as diabetes, hypertension, and obesity in future.

Many studies have been reported to improve care seeking behavior of mothers; complete vaccinations, intervention with supplementary food to improve protein, calorie, vitamin and mineral intake etc. However, none of these conventional therapeutic agents and methods has produced a visible impact on reducing stunting so far, and each of them have their own limitations and side-effects.

Dysbacteriosis (change in types or number of bacteria) is a term first described by Russian scientists more than a century ago, although there are mentions of similar problems in ancient Ayurveda as well. Dysbacteriosis in the gut in south Asian, African, and latin American countries is now considered to be playing a major role in giving rise to many nutritional disorders including stunting and poor neurocognitive development. Diarrhea (often chronic), along with macro- and micronutrient deficiency, and enteric enteropathy are believed to be cofactors in stunting. It is difficult to say if these factors separately, in sequence (one after other), or together drive stunting. This is particularly so, because many of these factors are present in the population that gets high rates of stunting. So, discerning the difference in terms of their contribution is difficult.

Although malnutrition points typically to under or over-nutrition (obesity), for the current disclosure, we have considered the term malnutrition for representing under nutrition, with the understanding that over-nutrition can also disrupt the normal intestinal flora. Recent studies in Africa have shown dysbacteriosis in children with under-nutrition. Elegant studies in human children and mice with transfer of stool samples have shown that indeed gut microbiota from sick and stunted children can produce stunting, neural defects, and problems with bone development and growth. (Blanton et al. *Gut bacteria that prevent growth impairments transmitted by microbiota from malnourished children. Science.* 2016 Feb. 19; 351(6275). pii: aad3311. doi: 10.1126/science.aad3311. PubMed PMID: 26912898).

Tropical Enteropathy (TE) is a condition where intestine of children (sometimes others) are deranged in terms of structure and function and there is inflammation. There is derangement of enzymes, but, the most important dysfunction is lower absorption and passage of nutrients out due to inflammation of the intestine by bombardment of with many bacteria from food and drinks in the contaminated environment. There is recent interest in addressing stunting by modulating TE (Naylor et al., *Environmental Enteropathy, Oral Vaccine Failure and Growth Faltering in Infants in Bangladesh. E Bio Medicine.* 2015 Sep. 25; 2(11):1759-66. doi: 10.1016/j.ebiom.2015.09.036. eCollection 2015 Nov.).

A recent study showed that there were drastic reduction in respiratory infections, blood infection called sepsis, and other infections including diarrhea, skin infections, and umbilical stump infection as provided in Panigrahi et al., A randomized synbiotic trial to prevent sepsis among infants in rural India. Nature. 2017 Aug. 24; 548 (7668): 407-412; Epub 2017 Aug. 16; PubMed PMID: 28813414.

There is an ongoing need in the art to develop newer and efficacious pharmaceutical compositions for treatment of stunting in children. The composition should also have benefits such as promoting gut maturation, enhancing gut health, enhancing protection later in life, and boosting of immune system.

OBJECTS OF THE INVENTION

An object of the present invention is to provide a pharmaceutical composition that can overcomes the deficiencies associated with the prior-art reported compositions.

Another object of the present invention to provide a pharmaceutical composition comprising a combination of a prebiotic and a probiotic.

Another object of the present invention to provide a method of preventing or treating stunting in children.

Another object of the present invention to provide a pharmaceutical composition that enhances gut health, enhancing protection later in life in children.

Another object of the present invention to provide a pharmaceutical composition that boost immune system in children.

Other objects of the present invention will be apparent from the description of the invention herein below.

SUMMARY OF THE INVENTION

The present invention relates to a pharmaceutical composition including a probiotic and a prebiotic for treating stunting. More particularly, the present invention relates to a composition including at least one *Lactobacillus* specie(s) as a probiotic and at least one oligosaccharide as a prebiotic for treating stunting in children. The present invention also relates to methods of treatment of stunting in children.

An aspect of the present disclosure provides a pharmaceutical composition for treatment of stunting in a subject, the composition comprising: a therapeutically effective amount of a probiotic; and an effective amount of a prebiotic. In an embodiment, the probiotic comprises at least one *Lactobacillus* species. In an embodiment, the prebiotic comprises at least one oligosaccharide. In an embodiment, the subject is a human of an age ranging from 0 month to 59 months. In an embodiment, the subject is a human of an age ranging from 0 month to 24 months. In an embodiment, the at least one *Lactobacillus* species is selected from a group comprising *L. acidophilus, L. casei, L. fermentum, L. salivarius, L. brevis, L. leichmannii, L. plantarum* and *L. cellobiosius*. In an embodiment, the probiotic comprises *Lactobacillus plantarum*. In an embodiment, the probiotic comprises *Lactobacillus plantarum* strain ATCC202195. In an embodiment, the at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof. In an embodiment, the at least one oligosaccharide comprises the fructo-oligosaccharide. In an embodiment, the composition is administered by any of an oral route of administration and a parenteral route of administration. In an embodiment, the composition comprises 1-10 billion counts of cells of *Lactobacillus plantarum* strain ATCC202195 and 100-500 mg of the fructo-oligosaccharide. The composition of the present disclosure provides a myriad of health benefits including, but not limited to, promoting gut maturation, enhancing gut health, enhancing protection later in life, promoting the maturation of the immune system, contributing to support of natural defences, contributing to support growth, enhancing gut comfort, fulfilling at least partially the nutritional requirements of children.

Another aspect of the present disclosure relates to a method of treating stunting in a subject in need thereof, the method comprising administering to the subject a therapeutically effective amount of a probiotic and an effective amount of a prebiotic. In an embodiment, the subject is a human of an age ranging from 0 month to 59 months. In an embodiment, the subject is a human of an age ranging from 0 month to 24 months. In an embodiment, the administering comprises oral or parenteral administration of said probiotic and said prebiotic. In an embodiment, the method comprises administering to the subject a composition comprising the therapeutically effective amount of the probiotic and the effective amount of the prebiotic. In an embodiment, the administering comprises simultaneous, sequential or intermittent administration of the therapeutically effective amount of the probiotic and the effective amount of the prebiotic. In an embodiment, the probiotic comprises at least one *Lactobacillus* species. In an embodiment, the prebiotic comprises at least one oligosaccharide. In an embodiment, the at least one *Lactobacillus* species is selected from a group comprising *L. acidophilus, L. casei, L. fermentum, L. salivarius, L. brevis, L. leichmannii, L. plantarum* and *L. cellobiosius*. In an embodiment, the at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof. In an embodiment, the therapeutically effective amount of the probiotic comprises 1-10 billion counts of cells of *Lactobacillus plantarum* strain ATCC202195 and the effective amount of the prebiotic comprises 100-500 mg of the fructo-oligosaccharide. In an embodiment, the therapeutically effective amount of the probiotic comprises 1-5 billion counts of cells of *Lactobacillus plantarum* strain ATCC202195 and the effective amount of the prebiotic comprises 150-350 mg of the fructo-oligosaccharide.

Still further aspect of the present disclosure relates to a method of treating dysbacteriosis in a subject in need thereof, the method comprising administering to the subject a therapeutically effective amount of a probiotic and an effective amount of a prebiotic. In an embodiment, the subject is a human of an age ranging from 0 month to 59 months. In an embodiment, the subject is a human of an age ranging from 0 month to 24 months. In an embodiment, the administering comprises oral or parenteral administration of said probiotic and said prebiotic. In an embodiment, the method comprises administering to the subject a composition comprising the therapeutically effective amount of the probiotic and the effective amount of the prebiotic. In an embodiment, the administering comprises simultaneous, sequential or intermittent administration of the therapeutically effective amount of the probiotic and the effective amount of the prebiotic. In an embodiment, the probiotic comprises at least one *Lactobacillus* species. In an embodiment, the prebiotic comprises at least one oligosaccharide. In an embodiment, the at least one *Lactobacillus* species is selected from a group comprising *L. acidophilus, L. casei, L. fermentum, L. salivarius, L. brevis, L. leichmannii, L. plantarum* and *L. cellobiosius*. In an embodiment, the at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof. In an embodiment, the therapeutically effective amount of the probiotic comprises 1-10 billion counts of cells of *Lactobacillus plantarum* strain ATCC202195 and the effective amount of the prebiotic comprises 100-500 mg of the fructo-oligosaccharide. In an embodiment, the therapeutically effective amount of the probiotic comprises 1-5 billion counts of cells of *Lactobacillus plantarum* strain ATCC202195 and the effective amount of the prebiotic comprises 150-350 mg of the fructo-oligosaccharide.

Various objects, features, aspects and advantages of the inventive subject matter will become more apparent from the following detailed description of preferred embodiments, along with the accompanying drawing figures in which like numerals represent like components.

DETAILED DESCRIPTION OF INVENTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The present invention relates to a pharmaceutical composition including a probiotic and a prebiotic for treating stunting. More particularly, the present invention relates to a composition including at least one *Lactobacillus* specie(s) as a probiotic and at least one oligosaccharide as a prebiotic for treating stunting in children. The present invention also relates to methods of treatment of stunting in children.

An aspect of the present disclosure provides a pharmaceutical composition for treatment of stunting in a subject, the composition comprising: a therapeutically effective amount of a probiotic; and an effective amount of a prebiotic. In an embodiment, the probiotic comprises at least one *Lactobacillus* species. In an embodiment, the prebiotic comprises at least one oligosaccharide. In an embodiment, the subject is a human of an age ranging from 0 month to 59 months. In an embodiment, the subject is a human of an age ranging from 0 month to 24 months. In an embodiment, the at least one *Lactobacillus* species is selected from a group comprising *L. acidophilus, L. casei, L. fermentum, L. salivarius, L. brevis, L. leichmannii, L. plantarum* and *L. cellobiosius*. In an embodiment, the probiotic comprises *Lactobacillus plantarum*. In an embodiment, the probiotic comprises *Lactobacillus plantarum* strain ATCC202195. In an embodiment, the at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof. In an embodiment, the at least one oligosaccharide comprises the fructo-oligosaccharide. In an embodiment, the composition is administered by any of an oral route of administration and a parenteral route of administration. In an embodiment, the composition comprises 1-10 billion counts of cells of *Lactobacillus plantarum* strain ATCC202195 and 100-500 mg of the fructo-oligosaccharide. In an embodiment, the composition comprises 1-5 billion counts of cells of *Lactobacillus plantarum* strain ATCC202195 and 150-350 mg of the fructo-oligosaccharide. In an embodiment, the composition further comprises at least one pharmaceutically acceptable excipient.

Accordingly, the composition of the present disclosure provides a myriad of health benefits including, but not limited to, promoting gut maturation, enhancing gut health, enhancing protection later in life, promoting the maturation of the immune system, contributing to support of natural defences, contributing to support growth, enhancing gut comfort, fulfilling at least partially the nutritional requirements of children.

Another aspect of the present disclosure relates to a method of treating stunting in a subject in need thereof, the method comprising administering to the subject a therapeutically effective amount of a probiotic and an effective amount of a prebiotic. In an embodiment, the subject is a human of an age ranging from 0 month to 59 months. In an embodiment, the subject is a human of an age ranging from 0 month to 24 months. In an embodiment, the administering comprises oral or parenteral administration of said probiotic and said prebiotic. In an embodiment, the method comprises administering to the subject a composition comprising the therapeutically effective amount of the probiotic and the effective amount of the prebiotic. In an embodiment, the composition further comprises at least one pharmaceutically acceptable excipient. In an embodiment, the administering comprises simultaneous, sequential or intermittent administration of the therapeutically effective amount of the probiotic and the effective amount of the prebiotic. In an embodiment, the probiotic comprises at least one *Lactobacillus* species. In an embodiment, the prebiotic comprises at least one oligosaccharide. In an embodiment, the at least one *Lactobacillus* species is selected from a group comprising *L. acidophilus, L. casei, L. fermentum, L. salivarius, L. brevis, L. leichmannii, L. plantarum* and *L. cellobiosius*. In an embodiment, the at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof. In an embodiment, the therapeutically effective amount of the probiotic comprises 1-10 billion counts of cells of *Lactobacillus plantarum* strain ATCC202195 and the effective amount of the prebiotic comprises 100-500 mg of the fructo-oligosaccharide. In an embodiment, the therapeutically effective amount of the probiotic comprises 1-5 billion counts of cells of *Lactobacillus plantarum* strain ATCC202195 and the effective amount of the prebiotic comprises 150-350 mg of the fructo-oligosaccharide.

Still further aspect of the present disclosure relates to a method of treating dysbacteriosis in a subject in need thereof, the method comprising administering to the subject a therapeutically effective amount of a probiotic and an effective amount of a prebiotic. In an embodiment, the subject is a human of an age ranging from 0 month to 59 months. In an embodiment, the subject is a human of an age ranging from 0 month to 24 months. In an embodiment, the administering comprises oral or parenteral administration of said probiotic and said prebiotic. In an embodiment, the method comprises administering to the subject a composition comprising the therapeutically effective amount of the probiotic and the effective amount of the prebiotic. In an embodiment, the composition further comprises at least one pharmaceutically acceptable excipient. In an embodiment, the administering comprises simultaneous, sequential or intermittent administration of the therapeutically effective amount of the probiotic and the effective amount of the prebiotic. In an embodiment, the probiotic comprises at least one *Lactobacillus* species. In an embodiment, the prebiotic comprises at least one oligosaccharide. In an embodiment, the at least one *Lactobacillus* species is selected from a group comprising *L. acidophilus, L. casei, L. fermentum, L. salivarius, L. brevis, L. leichmannii, L. plantarum* and *L. cellobiosius*. In an embodiment, the at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof. In an embodiment, the therapeutically effective amount of the probiotic comprises 1-10 billion counts of cells of *Lactobacillus plantarum* strain ATCC202195 and the effective amount of the prebiotic comprises 100-500 mg of the fructo-oligosaccharide. In an embodiment, the therapeutically effective amount of the probiotic comprises 1-5 billion counts of cells of

*Lactobacillus plantarum* strain ATCC202195 and the effective amount of the prebiotic comprises 150-350 mg of the fructo-oligosaccharide.

In one embodiment, the prebiotic includes one or more of the following (a) an oligosaccharide, (b) a fructo-oligosaccharide ("FOS"), such as a soy fructo-oligosaccharide, inulin or banana fiber, (c) a pectin or pectic polysaccharide, (d) a mannan, such as guar gum, locust bean gum, konjac, or xanthan gum, (e) a pentosan, beta-glucan, arabinan and galactan, such as larch arabinogalactan, and (f) mixtures thereof.

In a preferred embodiment, the prebiotic includes a fructo-oligosaccharide. The pharmaceutical composition of the present invention can be suitable for oral administration or parenteral route. In an embodiment, the pharmaceutical composition of the present invention can include 1-10 billion counts of cells of a probiotic and 100-500 mg of prebiotic. In an embodiment, the composition comprises 1-5 billion counts of cells of *Lactobacillus plantarum* strain ATCC202195 and 150-350 mg of the fructo-oligosaccharide. In an embodiment, the composition further comprises at least one pharmaceutically acceptable excipient. In an embodiment, the pharmaceutical composition of the present invention is administered to children of age between 0 to 59 months for prevention and treatment of stunting.

As utilized herein, the term "probiotic" refers to microorganisms that form at least a part of the transient or endogenous flora monoculture, and/or a mixed culture of living or dead microorganisms, spores, fractions thereof, or metabolic products thereof that exhibit a beneficial prophylactic and/or therapeutic effect on the host organism. Probiotics are beneficial bacteria that can be found in various foods, or in the form of dietary supplements.

Prebiotics are non digestible food ingredients that can stimulate growth of intestinal bacterial growth. The pharmaceutical compositions and methods of the present invention include one or more prebiotics in combination with one or more probiotics. In certain embodiments, these one or more prebiotics include, for example and without limitation, carbohydrates or oligosaccharides and polysachharides, more preferably oligo-fructose. Sources of oligosaccharides can include fruits, legumes, and whole grains.

Fructo-oligosaccharides (FOS) are long-chain polysaccharides comprised primarily of fructose monosaccharides bonded together by 1-β-D-fructofuranosyl linkages. Upon ingestion, fructo-oligosaccharides are only partially hydrolyzed as they pass through the mouth, stomach, and small intestine. In the large intestine, they became food for certain probiotics, and are metabolized into short chain fatty acids, mainly acetic, propionic, butyric, and lactic acids. As a consequence of this fermentation, a considerable amount of bacterial mass is produced. This results in increased numbers of probiotic, a lowered intestinal pH, and is believed to inhibit pathogens. A pH decrease will increase solubility of calcium and other minerals and may enhance the absorption of calcium and magnesium. Illustrative fructo-oligosaccharides include inulin, banana fiber, and soy fructo-oligosaccharides, and are found in honey, beer, onion, asparagus, Chinese chive, maple sugar, oats, and Jerusalem artichoke.

Examples of suitable probiotic micro-organisms can include but not limited to *Lactobacillus plantarum Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacil-2Q lus farciminus, Lactobacillus gasseri*, and *Lactobacillus helveticus.*

In one of the preferred embodiments of the present invention, the probiotic is *Lactobacillus plantarum*. More preferably, the probiotic is *Lactobacillus plantarum* strain ATCC 202195.

The growth of various *Lactobacillus* species to form cell cultures, cell pastes, and spore preparations is generally well-known within the art. The culture and preparative methods for *Lactobacillus plantarum* may be readily utilized and/or modified for growth and preparation of the other (lactic) acid-producing bacteria disclosed in the present invention.

Although exemplary of the present invention, *Lactobacillus plantarum* is utilized herein as a model for various other acid-producing (e.g., lactic acid) species of probiotic bacteria which may be useful in the practice of the present invention, and therefore is not to be considered as limiting.

The term "pharmaceutical composition", as used herein can be construed as but not limited to a nutritional composition, a nutraceutical composition, a nutritional supplement or a pharmaceutical drug.

The term "children or infants" as used herein refer to human beings of age between 0-59 months.

The term "therapeutically effective amount" as used herein means that amount of active ingredient (i.e. either probiotic or prebiotic or combination thereof) that elicits the biological or medicinal response in a subject which includes at least partial prevention or treatment of the symptoms of the disease being treated or prevented.

The term "effective amount of prebiotic" is art-recognized and used herein to denote that amount of prebiotic that supports the growth and/or maintenance of the probiotic being administered to the subject, such that the same in unison with the probiotic elicits the desired biological or medicinal response.

By "promoting gut maturation" is meant in particular (but not exclusively) maturation of the digestive system, including the related nervous system and immune system.

By "enhancing gut health" or by promoting "gut comfort" is meant in particular (but not exclusively) benefits selected from contributing to better balance the intestinal flora, reduce gut permeability, reducing cramps, reducing colics, increasing gut absorption or selectivity of absorption.

By "enhancing protection later in life" is meant in particular (but not exclusively) reducing the risk of infections and/or allergies later in life. The long term effect of probiotics (for example for protection against infections or protection against atopic diseases).

By "promoting the maturation of the immune system" is meant in particular (but not exclusively) growth and development of immune system.

By "contributing to support of natural defenses" is meant in particular (but not exclusively) enhancing the immune system, fighting infection, enhancing the maturation of the immune system.

By "contributing to support growth" is meant in particular (but not exclusively) enabling the growth of the infant or children to be as close as possible to the ideal growth curve.

The phrases "parenteral administration" and "administered parenterally" as used herein refer to modes of administration other than enteral and topical administration, such as injections, and include intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion, but not limited thereto.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The term "treating" or "treatment" is art recognized and includes prophylactic or therapeutic treatment including preventing a disease, disorder or condition from occurring in a human being or an animal, which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition also includes ameliorating at least one symptom of the particular disease or condition, even if the underlying pathophysiology is not affected, is well understood in the art, and includes administration of a composition which reduces the frequency of, or delays the onset of, symptoms of a medical condition in a subject relative to a subject which does not receive such composition. The term "prophylactic or therapeutic" treatment is art-recognized and includes administration to the host of one or more of the compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e. it is intended to diminish, ameliorate, or stabilize the existing unwanted condition or side effects thereof).

The phrase "pharmaceutically acceptable excipient" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

According to a preferred embodiment of the present invention, a prebiotic comprises one or more of the following (a) an oligosaccharide, (b) a fructo-oligosaccharide ("FOS"), such as a soy fructo-oligosaccharide, inulin or banana fiber, (c) a pectin or pectic polysaccharide, (d) a mannan, such as guar gum, locust bean gum, konjac, or xanthan gum, (e) a pentosan, beta-glucan, arabinan and galactan, such as larch arabinogalactan, and (f) mixtures thereof.

According to an embodiment, the pharmaceutical composition of the present disclosure may be administered in solid, semi-solid, or liquid oral dosage form. In an embodiment of the present disclosure, the pharmaceutical formulation can be in the form of emulsions, solutions, suspensions, syrups, elixirs, tablets, chewable tablets, capsules, pills, granules, and suppository. In another embodiment of the present disclosure, the pharmaceutical formulation can be in the form of water dispersible granules (WG), suspension concentrates (SC), wettable powders (WP), emulsifiable concentrates (EC), granules, gel, suspo emulsions (SE), mixed formulation of capsule suspension and suspension concentrates (ZC) and the like and preferably, water dispersible granules (WG), suspo emulsions (SE) and mixed formulation of capsule suspension and suspension concentrates (ZC).

In an embodiment, the pharmaceutical formulation of the present disclosure can be dried. Drying can include spray drying, fluid bed drying, or freeze-drying. In a preferred embodiment, the pharmaceutical formulation of the present disclosure is in an orally administered dosage form of powder or granule for sachet, liquid, solution, suspension, emulsion or syrup. In another embodiment of the present disclosure, the pharmaceutical formulation can include at least one pharmaceutically acceptable excipient selected from the group consisting of fillers, binders, diluents, thickening agents, solvents, coating agents, dispersing agents, preservatives, sweeteners, flavoring agents, antifoaming agent and stabilizers. However, those skilled in the art will appreciate that the additional pharmaceutically acceptable excipients can be used without departing from the scope and spirit of the present disclosure.

Pharmaceutically acceptable filler may be selected from the group comprising lactose, microcrystalline cellulose, starch, pre-gelatinized starch, calcium phosphate, calcium sulfate, calcium carbonate, mannitol, sorbitol, xylitol, sucrose, maltose, fructose, dextrose, maltodextrin, and the like. Pharmaceutically acceptable binder may be selected from the group comprising starches, natural sugars, corn sweeteners, natural and synthetic gums, cellulose derivatives, gelatin, povidone, polyethylene glycol, waxes, sodium alginate, alcohols, water, and the like. Pharmaceutically acceptable diluents may be selected from the group comprising calcium carbonate, calcium phosphate dibasic, calcium phosphate tribasic, calcium sulfate, microcrystalline cellulose, microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, maltose maltodextrin, maltitol, and the like. Pharmaceutically acceptable sweetener may be selected from the group comprising alitame, acesulfame potassium, aspartame, D-tryptophan, dextrose, erythritol, fructose, galactose, glycerol, glycyrrhizin, glucose, isomalt, xylitol, xylose, lactitol, lactose, levulose, maltitol, maltodextrin, maltol, maltose, mannitol, corn syrup, neohesperidin dihydrochalcone, neotame, saccharin, siclamate, sorbitol, sucralose, sucrose, tagatose, taumatin, trehalose, and the like. Pharmaceutically acceptable flavoring agent may be selected from the group comprising natural flavoring oils, anethole, acetic acid, ascorbic acid, phosphoric acid, fumaric acid, lactic acid, lemon, linalool, malic acid, menthol, eucalyptol, orange, citric acid, cinnamone, tartaric acid, thymol, vanilla, strawberry, and the like. Pharmaceutically acceptable preservative may be selected from the group comprising parabens, phenol, chlorocresol, parahydroxy benzoic acid alkyl esters, benzoic acid and salts thereof, boric acid and salts thereof, citric acid and salts thereof, sorbic acid and salts thereof, neutral preservatives, mercurial preservatives, quaternary compounds, and the like.

In yet another embodiment, the pharmaceutical composition of the present invention can be administered by parenteral route such as intravenous administration. In an embodiment, the pharmaceutical composition of the present invention can include 1-10 billion count of cells of a probiotic and 100-500 mg of a prebiotic. In an embodiment, the composition comprises 1-5 billion counts of cells of *Lactobacillus plantarum* strain ATCC202195 and 150-350 mg of the fructo-oligosaccharide.

According to another embodiment, the pharmaceutical composition of the present invention may be administered in solid or liquid oral dosage form such as emulsions, solutions, suspensions, syrups, elixirs, tablets, chewable tablets, capsules, pills, granules, and suppository.

In an embodiment, the composition may be in the form of granules, powdered supplements (such as a supplement that can be mixed with a drink), reconstitutable powders (spray dried, dry mixed, agglomerated), ready-to-feed liquids, bars, and dilutable liquid concentrates and the likes. However, any other solid, liquid or semi-solid composition or formulation, as known to or appreciated by a person skilled in the art, can be utilized to serve its intended purpose, as laid in the present disclosure, without departing from the scope and spirit of the present invention.

For parenteral administration, solutions (compositions) may be prepared using (for example) sesame or peanut oil, aqueous propylene glycol, or sterile aqueous solutions. Such solutions may be suitably buffered if necessary, and the liquid diluent is first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The compositions of the present invention are preferably presented for administration to humans and animals in unit dosage forms, such as tablets, capsules, pills, powders, granules, suppositories, sterile parenteral solutions or suspensions, sterile non-parenteral solutions, suspensions, and oral solutions or suspensions and the like, containing suitable quantities of an active ingredient. For oral administration either solid or fluid unit dosage forms can be prepared.

In an embodiment, the tablet core contains one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants or mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof. Suitable lubricants include, but are not limited to, long chain fatty acids and their hydrates or solvates, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their hydrates or solvates, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate hydrates or solvates, and mixtures thereof. Examples of preservatives include, but are not limited to, citric acid, tartaric acid, lactic acid, malic acid, acetic acid, benzoic acid, and sorbic acid, and mixtures thereof.

In one embodiment, the immediate release coating has an average thickness of at least 50 microns, such as from about 50 microns to about 2500 microns; e.g., from about 250 microns to about 1000 microns. In embodiment, the immediate release coating is typically compressed at a density of more than about 0.9 g/cc, as measured by the weight and volume of that specific layer.

In one embodiment, the immediate release coating contains a first portion and a second portion, wherein at least one of the portions contains the second pharmaceutically active agent. In one embodiment, the portions contact each other at a center axis of the tablet. In one embodiment, the first portion includes the first pharmaceutically active agent and the second portion includes the second pharmaceutically active agent.

In one embodiment, the first portion contains the first pharmaceutically active agent and the second portion contains the second pharmaceutically active agent. In one embodiment, one of the portions contains a third pharmaceutically active agent. In one embodiment one of the portions contains a second immediate release portion of the same pharmaceutically active agent as that contained in the tablet core.

In one embodiment, the outer coating portion is prepared as a dry blend of materials prior to addition to the coated tablet core. In another embodiment the outer coating portion is included of a dried granulation including the pharmaceutically active agent.

Formulations with different drug release mechanisms described above could be combined in a final dosage form containing single or multiple units. Examples of multiple units include multilayer tablets, capsules containing tablets, beads, or granules in a solid or liquid form. Typical, immediate release formulations include compressed tablets, gels, films, coatings, liquids and particles that can be encapsulated, for example, in a gelatin capsule. Many methods for preparing coatings, covering or incorporating drugs, are known in the art.

The immediate release dosage, unit of the dosage form, i.e., a tablet, a plurality of drug-containing beads, granules or particles, or an outer layer of a coated core dosage form, contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads).

Extended release formulations are generally prepared as diffusion or osmotic systems, for example, as described in "Remington—The Science and Practice of Pharmacy", 20th. Ed., Lippincott Williams & Wilkins, Baltimore, Md., 2000. A diffusion system typically consists of one of two types of devices, reservoir and matrix, which are well known and described in the art. The matrix devices are generally prepared by compressing the drug with a slowly dissolving polymer carrier into a tablet form.

An immediate release portion can be added to the extended release system by means of either applying an immediate release layer on top of the extended release core; using coating or compression processes or in a multiple unit system such as a capsule containing extended and immediate release beads.

Delayed release dosage formulations are created by coating a solid dosage form with a film of a polymer, which is insoluble in the acid environment of the stomach, but soluble in the neutral or slightly basic environment of small intestine. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule.

A pulsed release dosage form is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

Each dosage form contains any or a combination of a therapeutically effective amount of probiotic and an effective amount of prebiotic (each of the "probiotic" and "prebiotic", independently, are alternatively and synonymously referred to as "active agent" or "active ingredient" herein through the present disclosure). In one embodiment of dosage forms that mimic a twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 30 wt. %, preferably 60 wt. % to 40 wt. %, of the total amount of active agent in the dosage form is released in the second pulse. For dosage forms mimicking the twice daily dosing profile, the second pulse is preferably released approximately 3 hours to less than 14 hours, and more preferably approximately 5 hours to 12 hours, following administration.

Another dosage form contains a compressed tablet or a capsule having a drug-containing immediate release dosage unit, a delayed release dosage unit and an optional second delayed release dosage unit. In this dosage form, the immediate release dosage unit contains a plurality of beads, granules particles that release drug substantially immediately following oral administration to provide an initial dose. The delayed release dosage unit contains a plurality of coated beads or granules, which release drug approximately 3 hours to 14 hours following oral administration to provide a second dose.

Methods of preparing various pharmaceutical compositions of the present disclosure are well within the reach of those skilled in this art. For examples of methods of preparing pharmaceutical compositions, see Remington's Pharmaceutical Sciences, Mack Publishing Company, Easton, Pa., 19th Edition (1995).

In addition, in certain embodiments, subject compositions of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Methods of preparing these formulations or compositions include the step of bringing into association compound with the carrier and, optionally, one or more accessory ingredients. In general, the formulations are prepared by uniformly and intimately bringing into association a compound with liquid carriers, or finely divided solid carriers, or both, and then, if necessary, shaping the product.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the active ingredient, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, or mixtures thereof.

In an embodiment, each of the prebiotic and probiotic can be prepared as separate formulations (such as tablets, capsules, powder and the likes) and the same can be orally administered to the subject in need thereof. Each of the prebiotic and probiotic can be administered (such as orally ingested) simultaneously, sequentially or intermittently so far the beneficial effects of each of the prebiotic and the probiotic are maintained, as disclosed herein. It should also be appreciated that any other active ingredient, herb, neutraceutical, or excipient, as known to or appreciated by a person skilled in the pertinent art, can be co-administered with the composition(s) and/or included in the compositions of the present disclosure, without departing from the scope and spirit of the present disclosure. The term "co-administer" means to administer more than one active agent, such that the duration of physiological effect of one active agent overlaps with the physiological effect of a second active agent. In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In one embodiment, the prebiotic and the probiotic are formulated into a single formulation (such as a tablet, capsule or powder that includes both the required dosage of prebiotic as well as the required dosage of probiotic). The formulation that includes both the required dosage of prebiotic as well as the required dosage of probiotic can be a single dosage formulation or a multiple dosage formulation.

In an embodiment, a combination of 1 billion count of cells of *L. plantarum* and about 150 mg of fructo-oligosaccharides, with or without one or a combination of excipients such as maltodextrin, is mixed with 1-2 ml of saline solution or dextrose saline solution (5% DNS) or other suitable carrier liquid and can be orally fed once a day to a newborn infant starting from day 2 (i.e. orally fed to human infant of age of 2 days) and fed daily for 7 days (one week). The same treatment regimen can be followed for $2^{nd}$ Month i.e. a mixture of 1 billion count of cells of *L. plantarum* and about 150 mg of fructo-oligosaccharides, with or without one or a combination of excipients such as maltodextrin, can be mixed with 1-2 ml of saline solution or dextrose saline solution (5% DNS) or other suitable carrier liquid and can be orally fed once a day for one week. For $3^{rd}$, $4^{th}$ and $5^{th}$ Month, a mixture of 2 billion count of cells of *L. plantarum* and about 150 mg of fructo-oligosaccharides, with or without one or a combination of excipients such as maltodextrin, can be mixed with 1-2 ml of saline solution or dextrose saline solution (5% DNS) or other suitable carrier liquid and can be orally fed once a day for one week. For $6^{th}$ Month through $12^{th}$ Month, a mixture of 4 billion count of cells of *L. plantarum* and about 300 mg of fructo-oligosaccharides, with or without one or a combination of excipients such as maltodextrin, can be mixed with 3 ml of saline solution or dextrose saline solution (5% DNS) or other suitable carrier liquid and can be orally fed once a day for one week. For $13^{th}$ Month through $24^{th}$ Month, a mixture of 5 billion count of cells of *L. plantarum* and about 500 mg of fructo-oligosaccharides, with or without one or a combination of excipients such as maltodextrin, can be mixed with 5 ml of saline solution or dextrose saline solution (5% DNS) or other suitable carrier liquid and can be orally fed once a day for one week. Alternatively, the composition(s) of the present disclosure can be administered following any other suitable treatment regimen to derive the beneficial effects as disclosed in the present application, without departing from the scope and spirit of the present disclosure. Appropriateness of such treatment regimen can be determined and/or suitable treatment regimen can be selected (including dosage, frequency of administration, route of administration, or any change therein) by a medical practitioner based on one or a combination of parameters such as age of the child/infant, ethnicity, co-morbidity (such as diarrhea, vomiting and the likes), patient compliance and the likes and all such variations in the therapeutic/treatment regimen are to be treated as part and parcel of the present disclosure without departing from the scope and spirit of the present invention.

The composition of the present disclosure can provide a myriad of health benefits including, but not limited to, promoting gut maturation, enhancing gut health, enhancing protection later in life, promoting the maturation of the immune system, contributing to support of natural defenses, contributing to support growth, enhancing gut comfort, fulfilling at least partially the nutritional requirements of children.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

Composition including *Lactobacillus plantarum* ATCC 202195 and Fructo-Oligosaccharides Powdered formulations, as shown in Table 1 below, each including *Lactobacillus plantarum* ATCC 202195, fructo-oligosaccharides and maltodextrin were prepared.

TABLE 1

Powdered Formulations

| Formulation No. | L. plantarum ATCC 202195 (count of cells in billions per formulation) | Fructo-oligosaccharides (mg per formulation) | maltodextrin (mg per formulation) |
|---|---|---|---|
| 1 | 1 | 150 | 350 |
| 2 | 2 | 150 | 350 |
| 3 | 4 | 300 | 350 |
| 4 | 5 | 500 | 350 |

Each of the aforesaid formulations 1 through 4 were packed in sachets and stored in cool moisture proof containers for further usage.

Administration of *Lactobacillus plantarum* ATCC 202195 and Fructo-Oligosaccharides to Infants A cohort of infants were orally fed with a synbiotic preparation containing *Lactobacillus plantarum* ATCC 202195 and fructo-oligosaccharides after birth. In the randomized controlled trial, half of the infants were kept as controls with placebo. Each of the infants (treatment group, referred to herein as "symbiotic-treated") was orally fed with formulation 1 mixed with 1-2 ml of 5% dextrose saline solution (5% DNS) once a day starting from day 2 (i.e. orally fed to human infant of age of 2 days) for 7 days (one week). The same treatment was repeated for $2^{nd}$ Month i.e. orally fed with formulation 1 mixed with 1-2 ml of 5% dextrose saline solution (5% DNS) once a day for one week. For $3^{rd}$, $4^{th}$ and $5^{th}$ Month, each of the infants were orally fed with formulation 2 mixed with 1-2 ml of 5% dextrose saline solution (5% DNS) once a day for one week in each of $3^{rd}$, $4^{th}$ and $5^{th}$ month. For $6^{th}$ Month through $12^{th}$ Month, each of the infants were orally fed with formulation 3 mixed with 3 ml of 5% dextrose saline solution (5% DNS) once a day for one week in each of $6^{th}$ through $12^{th}$ month. For $13^{th}$ through $24^{th}$ Month, each of the infants were orally fed with formulation 4 mixed with 5 ml of 5% dextrose saline solution (5% DNS) once a day for one week in each of $13^{th}$ through $24^{th}$ month.

A three tier structure was followed with trained personnel in the field where each village had a trained CHV (community health volunteer) supervised by managers and supervisors who reported to physicians in the attached hospitals, and ultimately headed by the PI (principal investigator) for the two sites (Rourkela and Bhubaneswar). 601 infants were randomly selected from the villages where the study was done and measurements of weight, and height at two years of age (24 months±3 months) were done. Mother's age at the time of child birth was also recorded, since teen-age pregnancy and after the age 40 are known to have adverse pregnancy outcomes, which can contaminate the health status of the newborn in the first years of life. Height and weight measurements were converted into age- and sex-specific z-scores based on WHO child growth standards (WHO, 2007). Stunting was defined as any z-score below (−2) standard deviations. Table 2 below provides Characteristics of study participants (total number of participants were 601).

TABLE 2

Characteristics of study participants (n = 601)

| | Placebo (n = 305) | Synbiotic-treated (n = 296) |
|---|---|---|
| Infant Birth Weight (mean ± standard deviation, sd) | 2831 ± 358 | 2811 ± 367 |
| No. of Child - Male | 164 | 170 |
| No. of Child - Female | 141 | 126 |
| Child Height in cm (mean ± sd) | 81.23 ± 4.56 | 82.21 ± 4.69 |
| Child Weight in Kg (mean ± sd) | 10.12 ± 1.46 | 10.70 ± 1.72 |
| Mother's age (in yrs) at birth of the baby | 25.08 ± 3.35 | 25.18 ± 3.9 |

The birth weight, height, and weight were normally distributed in the two groups. Mean mother's age was also almost identical (25 years) in the study population confirming that other major maternal factors were not playing a role. Although food, water, and environmental factors could be playing some roles, in this 1:1 placebo:synbiotic allocation, all these factors would be equally distributed between the two groups nullifying any impact.

Mean height and weight of children in this cohort also appeared to be similar between the two groups. However, after computing height-for-age and weight-for-height, the patterns as reported in Table 3 below emerged. The two groups were compared by chi-square test.

TABLE 3

Prevalence of stunting and wasting in
children at 24 months of age (n = 601)

|  | Placebo (n = 305) | Treatment (n = 296) | p value |
|---|---|---|---|
| Stunting (height-for-age; WHO 2007) | | | |
| Stunted | 128 | 93 | 0.006* |
| Normal | 177 | 203 | |
| Wasting (weight-for-height; WHO 2007) | | | |
| Wasted | 58 | 45 | 0.215 |
| Normal | 247 | 251 | |

In conclusion, significant reduction in stunting in the symbiotic-treated infants (p=0.006) was observed as compared to placebo recipients. These surprising results demonstrated for the first time that oral administration of synbiotics, and specifically, a combination of *Lactobacillus plantarum* (strain ATCC202195) and a prebiotic, to infants early in life reduces the rate of stunting at two years of age. It was further intriguing to note that wasting was not affected by such a treatment (p=0.2). Together, these results show for the first time that the synbiotics used in this study work in a unique manner to treat the dysbacteriosis, which in turn, prevents/reduces stunting in a statistically significant manner. Since the first two years of life are considered most important, a period in which the "die casting" is done for the child, such treatment help protects the infants from long term health squeal including cognitive impairments.

Advantages

The present invention provides a pharmaceutical composition that can overcomes the deficiencies associated with the prior-art reported compositions.

The present invention provides a pharmaceutical composition comprising a combination of a prebiotic and a probiotic.

The present invention provides a method of treating stunting in children.

The present invention provides a pharmaceutical composition that enhances gut health, enhancing protection later in life in children.

The present invention provides a pharmaceutical composition that boost immune system in children.

We claim:

1. A method of treating stunting in a subject in need thereof, the method comprising administering to the subject an effective amount of a probiotic and an effective amount of a prebiotic, wherein the subject is a human subject aged 0 to 59 months.

2. The method as claimed in claim 1, wherein the administering comprises oral or parenteral administration of said probiotic and said prebiotic.

3. The method as claimed in claim 1, wherein the method comprises administering to the subject a composition comprising the effective amount of the probiotic, the effective amount of the prebiotic, and a suitable excipient.

4. The method as claimed in claim 1, wherein the administering comprises simultaneous, sequential or intermittent administration of the effective amount of the probiotic and the effective amount of the prebiotic.

5. The method as claimed in claim 1, wherein said probiotic comprises at least one *Lactobacillus* species, and wherein said prebiotic comprises at least one oligosaccharide.

6. The method as claimed in claim 1, wherein said at least one *Lactobacillus* species is selected from a group comprising *L. acidophilus, L. casei, L. fermentum, L. salivarius, L. brevis, L. leichmannii, L. plantarum* and *L. cellobiosius*, and wherein said at least one oligosaccharide is selected from a group comprising (a) a fructo-oligosaccharide (FOS), (b) a pectin or a pectic polysaccharide, (c) a mannan, (d) a pentosan, a beta-glucan, an arabinan or a galactan, and (e) mixtures thereof.

7. The method as claimed in claim 1, wherein the effective amount of the probiotic comprises 1-10 billion counts of cells of *Lactobacillus plantarum* strain ATCC202195 and wherein the effective amount of the prebiotic comprises 100-500 mg fructo-oligosaccharide.

8. The method as claimed in claim 1, wherein the effective amount of the prebiotic comprises a fructo-oligosaccharide.

9. The method as claimed in claim 1, wherein said subject is a human subject aged 0 to 24 months.

\* \* \* \* \*